(12) United States Patent
Lee et al.

(10) Patent No.: US 9,829,426 B2
(45) Date of Patent: Nov. 28, 2017

(54) FLUID ANALYSIS SHEET, FLUID ANALYSIS CARTRIDGE INCLUDING THE SAME, AND METHOD OF MANUFACTURING FLUID ANALYSIS CARTRIDGE

(71) Applicant: SAMSUNG ELECTRONICS CO., LTD., Suwon-si (KR)

(72) Inventors: Seung Jun Lee, Yongin-si (KR); Jung Ki Min, Yongin-si (KR); Seung Hoon Kim, Suwon-si (KR); Ji Young Park, Seoul (KR); Hyun-Suk Kang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 104 days.

(21) Appl. No.: 14/743,437

(22) Filed: Jun. 18, 2015

(65) Prior Publication Data
US 2015/0369745 A1 Dec. 24, 2015

(30) Foreign Application Priority Data

Jun. 24, 2014 (KR) .................. 10-2014-0077604

(51) Int. Cl.
*G01N 21/75* (2006.01)
*G01N 21/03* (2006.01)
*G01N 21/78* (2006.01)

(52) U.S. Cl.
CPC ............ *G01N 21/03* (2013.01); *G01N 21/78* (2013.01); *G01N 2021/0325* (2013.01); *Y10T 156/1052* (2015.01)

(58) Field of Classification Search
CPC .......... G01N 21/03; G01N 2021/0325; G01N 21/78; Y10T 156/1052
See application file for complete search history.

(56) References Cited

U.S. PATENT DOCUMENTS

| 2002/0098124 A1* | 7/2002 | Bentsen | B01L 3/502707 422/502 |
| 2008/0314745 A1* | 12/2008 | Neubert | C12Q 1/001 204/403.01 |
| 2014/0017124 A1* | 1/2014 | Lee | G01N 35/00 422/69 |

FOREIGN PATENT DOCUMENTS

| KR | 10-2002-0000767 A | 1/2002 |
| KR | 10-2005-0086919 A | 8/2005 |

OTHER PUBLICATIONS

Glavan, et al.; "Rapid Fabrication of Pressure-Driven Open-Channel Microfluidic Devices in Omniphobic $R^F$ Paper", Royal Society of Chemistry, Lab Chip, May 10, 2013, vol. 13, 9 pages total (pp. 2922-2930).

* cited by examiner

*Primary Examiner* — Dennis M White
(74) *Attorney, Agent, or Firm* — Sughrue Mion, PLLC

(57) ABSTRACT

Provided is a fluid analysis cartridge configured to analyze a fluid specimen, a fluid analysis sheet forming the same and a method of manufacturing the fluid analysis cartridge. The fluid analysis sheet includes at least one cut out part configured to form an intermediate layer of an inspection substrate, the cut out part including a flow passage structure including an inlet part in which a fluid is introduced and an inspection part in which the fluid is introduced to react with a reagent; and wherein the cut out part is further configured to include a first end adjacent to the inspection part and a second end adjacent to the inlet part, and wherein a minimum distance between the first end and the flow passage structure is at least 1 mm.

25 Claims, 11 Drawing Sheets

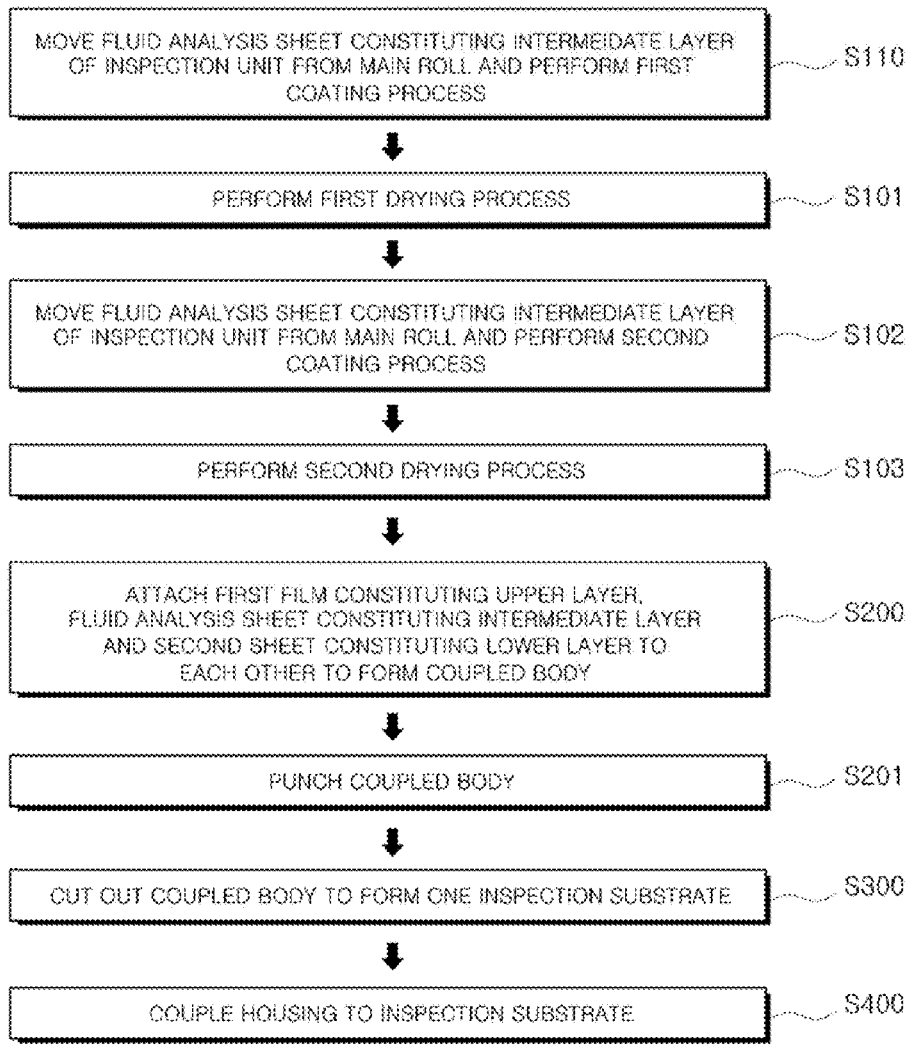

FLUID ANALYSIS SHEET, FLUID ANALYSIS CARTRIDGE INCLUDING THE SAME, AND METHOD OF MANUFACTURING FLUID ANALYSIS CARTRIDGE

CROSS-REFERENCE TO RELATED APPLICATION

This application claims priority from Korean Patent Application No. 10-2014-0077604 filed on Jun. 24, 2014, in the Korean Intellectual Property Office, the disclosure of which is incorporated herein by reference.

BACKGROUND

1. Field

Apparatuses and methods consistent with exemplary embodiments relate to a fluid analysis cartridge configured to analyze a fluid specimen, a fluid analysis sheet used in forming the fluid analysis cartridge, and a method of manufacturing the fluid analysis cartridge.

2. Description of the Related Art

In various fields such as environmental monitoring, food inspection, and medical diagnosis, a device and a method of analyzing a fluid specimen have been required. In the related art, in order to perform an inspection according to a fixed protocol, a skilled experimenter should manually perform steps such as reagent injection, mixing, separation, transferring, reaction and centrifugation, several times. This process can lead to an error of the inspection result.

In order to improve the above situation, miniaturized and automated equipment which can rapidly analyze substances to be inspected have been developed. In particular, a portable fluid analysis cartridge can quickly analyze fluid specimen regardless of a place. If a function and performance thereof are improved, the fluid analysis cartridge can perform more diverse functions in more diverse fields. Therefore, research and development on this are required. In addition, performance improvement can allow an unskilled experimenter to also easily perform an inspection.

In related art, foreign substances may be generated on a contact portion at which the fluid analysis cartridge is in contact with the fluid analysis device, and thus these foreign substances may influence an inspection result. Therefore, it is necessary to prevent such foreign substances from being generated or entering into the fluid analysis area.

In addition, in a method of manufacturing the fluid analysis cartridge, in a case in which the fluid specimen is a hydrophilic fluid, there is a need to coat at least a portion of an inspection substrate constituting the fluid analysis cartridge with a hydrophobic solution. If the coating is not achieved well, reliability of the inspection may be degraded.

SUMMARY

One or more exemplary embodiments provide a fluid analysis sheet having a structure so that reliability of an inspection may be increased, a fluid analysis cartridge including the fluid analysis sheet, and a method of manufacturing the fluid analysis cartridge.

According to an aspect of an exemplary embodiment, there is provided a fluid analysis sheet at least one cut out part configured to form an intermediate layer of an inspection substrate, the cut out part including: a flow passage structure including an inlet part in which a fluid is introduced and an inspection part in which the fluid is introduced to react with a reagent; and wherein the cut out part is further configured to include a first end adjacent to the inspection part and a second end adjacent to the inlet part, and wherein a minimum distance between the first end and the flow passage structure is at least 1 mm.

The first end may include at least one dent part, the dent part oriented toward the second end.

The dent part may be formed to have a pattern.

The dent part may formed in a circular shape.

The dent part may be formed in a quadrangular shape.

The first end may include a first contact part formed in a curved shape and a second contact part formed in a linear shape.

The minimum distance between the first contact part and the flow passage structure may be at least 1 mm.

The minimum distance between the second contact part and the flow passage structure may be at least 2 mm.

The fluid analysis sheet may have a surface which is coated with a hydrophobic solution to prevent a hydrophilic fluid from being spread therein.

According to an aspect of another exemplary embodiment, there is provided a fluid analysis cartridge, including: a housing including at least one supplying hole to supply a fluid specimen; and an inspection substrate coupled to the housing such that the fluid specimen introduced through the supplying hole is introduced to be inspected, wherein the inspection substrate includes: an upper layer located at an upper side; a lower layer located at a lower side; and an intermediate layer located between the upper layer and the lower layer, and coupled to the upper layer and the lower layer such that at least a portion of an end of the intermediate layer is located inside with respect to an edge of the upper layer and an edge of the lower layer.

The intermediate layer may have a flow passage structure that includes an inlet part in which a fluid is introduced; and an inspection part in which the fluid is introduced to react with a reagent.

The first end of the intermediate layer may be adjacent to the inspection part, and the first end is provided with a dent part oriented such that at least a portion of the dent part is dented inward from the first end.

The dent part may be formed to have a pattern.

The dent part may be formed in a circular shape and a minimum distance between the dent part and the flow passage structure is at least 1 mm.

The dent part may be formed in a quadrangular shape and a minimum distance between the dent part and the flow passage structure is at least 2 mm.

The surface of the intermediate layer may be coated with a hydrophobic solution to prevent a hydrophilic fluid from being spread therein.

According to another exemplary embodiment, there is provided a method of manufacturing a fluid analysis cartridge including an inspection substrate in which a fluid is inspected, the inspection substrate including an upper layer, an intermediate layer and a lower layer, and the fluid analysis cartridge further including a housing coupled to the inspection substrate, the method including: moving a fluid analysis sheet constituting the intermediate layer of the inspection substrate from a main roll; performing first and second coating processes to coat the fluid analysis sheet with a hydrophobic solution; attaching an upper film constituting the upper layer, the fluid analysis sheet constituting the intermediate layer and a lower film constituting the lower layer to each other to form a coupled body; cutting out the coupled body to form one inspection substrate; and coupling the housing to the inspection substrate.

The fluid analysis sheet may be wound around a first coating roll and a second coating roll when at least one of the first and second coating processes is performed.

A first drying process and a second drying process may be performed after each of the first and second coating process is performed.

The hydrophobic solution may include at least one of fluorinated acrylic copolymer, fluorocarbon, silicone and a fluorocarbon-silicon coupling agent.

The coupled body may be formed by attaching double-sided tapes on an upper surface and a lower surface of the fluid analysis sheet.

The coupled body may be cut off such that the intermediate layer is located inside with respect to at least one edge of the upper layer and at least one edge of the lower layer.

The intermediate layer may include a dent part oriented such that at least a portion of the dent part is dented inward from an edge so as to be formed to be located inside with respect to an edge of the upper layer and an edge of the lower layer, and the method includes forming the dent part before the coupled body is cut.

An exemplary embodiment of the flow analysis sheet may include a plurality of the cut out parts arranged in at least one of: two columns and two rows.

An exemplary embodiment of the flow analysis sheet may be formed from a porous material.

An exemplary embodiment of the fluid analysis cartridge may have the intermediate layer formed from a porous material; and the upper layer and the lower layer may be formed from a chemically and biologically inactive film.

BRIEF DESCRIPTION OF THE DRAWING

The above and/or other aspects will become apparent and more readily appreciated from the following description of exemplary embodiments, taken in conjunction with the accompanying drawings in which:

FIG. 11 is a flow chart concretely illustrating a method of manufacturing a fluid analysis cartridge according to an exemplary embodiment.

DETAIL DESCRIPTION

Hereinafter, a fluid analysis sheet according to an exemplary embodiment and a fluid analysis cartridge including the same are described with reference to the accompanying drawings. Also, an embodiment of a method of manufacturing the fluid analysis cartridge will be described.

Figure 1:
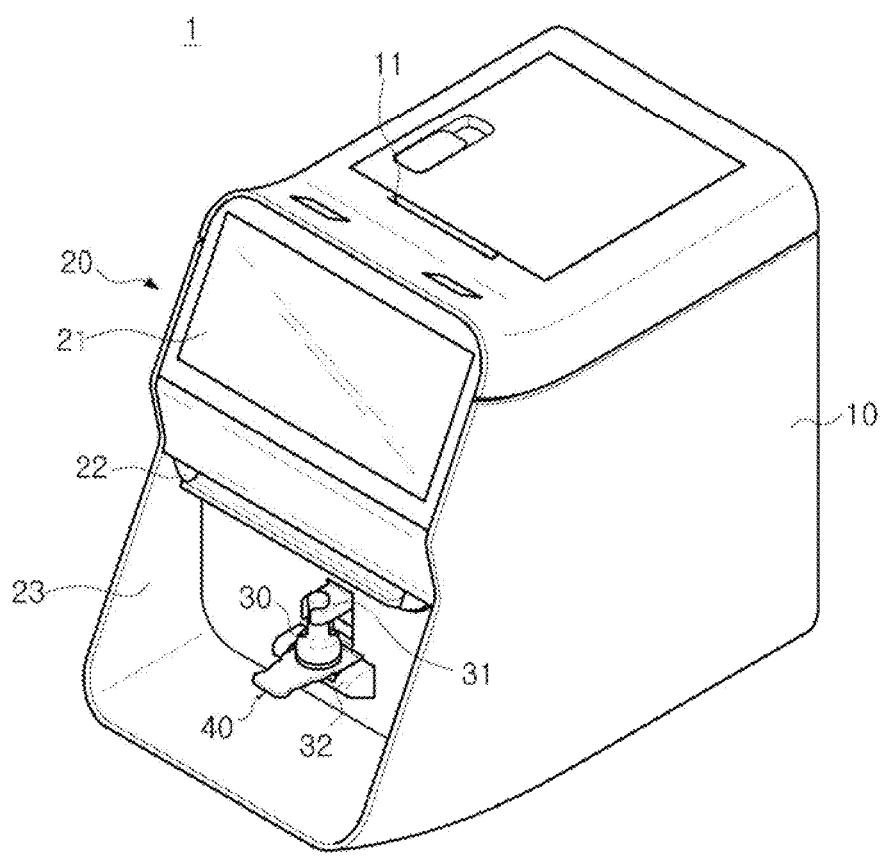
FIG. 1 is a view illustrating a fluid analysis device to which a fluid analysis cartridge according to an exemplary embodiment is coupled.

FIG. 1 is a view illustrating a fluid analysis device to which the fluid analysis cartridge according to an exemplary embodiment is coupled.

As shown in FIG. 1, a fluid analysis device 1 to which a fluid analysis cartridge 40 according to an exemplary embodiment is coupled includes a housing 10 forming an outer appearance and a door module 20 provided in the front of the housing 10.

The door module 20 may include a display part 21, a door 22 and a door frame 23. The display part 21 and the door 22 may be arranged in the front of the door frame 23. The display part 21 may be located above the door 22. The door 22 may be slidably provided. When the door 22 is slid and opened, the door 22 is provided to be located behind the display part 21.

The information on specimen analysis content, a specimen analyzing operation status and the like may be displayed on the display part 21. The door frame 23 may be provided with a mounting member 32 to which the fluid analysis cartridge 40 may be mounted. Here, a fluid specimen is accommodated in the fluid analysis cartridge 40. A user slides the door 22 upward to open the door 22, and then mounts the fluid analysis cartridge 40 to the mounting member 32. Then, the user slides the door 22 downward to close the door 22 and perform an analysis operation.

The fluid specimen is introduced into the fluid analysis cartridge 40 and is then reacts with a reagent in an inspection substrate 45. The fluid analysis cartridge 40 is inserted into the mounting member 32 and a pressurizing member 31 pressurizes the fluid analysis cartridge 40 via covering member 30 to enable the fluid specimen in the fluid analysis cartridge 40 to be introduced into the inspection substrate 45.

Apart from the display part 21, the fluid analysis device may be further provided with an output part 11 configured to output an inspection results as separate printed matter.

Figure 2:
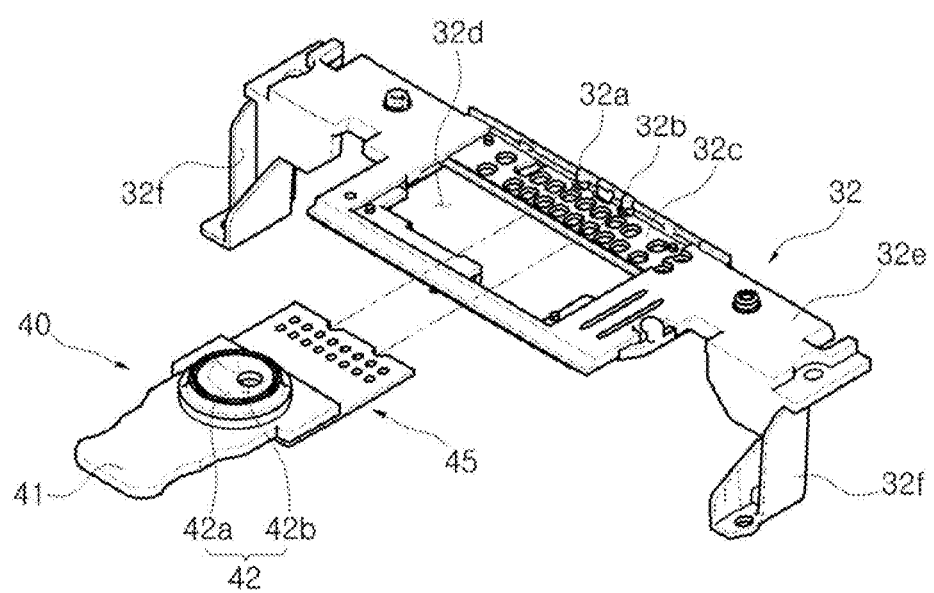
FIG. 2 is a view illustrating a state in which a fluid analysis cartridge according to an exemplary embodiment is uncoupled from a mounting member of a fluid analysis device to which the fluid analysis cartridge is coupled during analysis.
Figure 3:
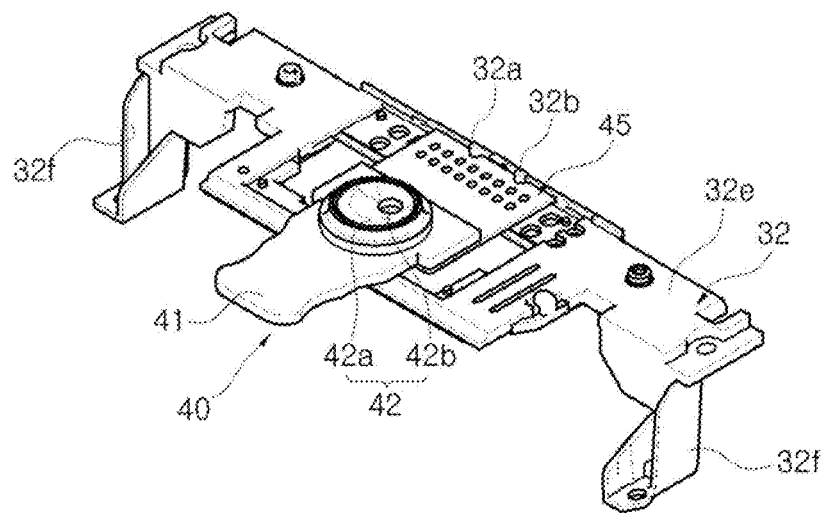
FIG. 3 is a view illustrating a state in which a fluid analysis cartridge according to an exemplary embodiment is coupled to a mounting member of a fluid analysis device to which the fluid analysis cartridge is coupled during analysis.
Figure 4:
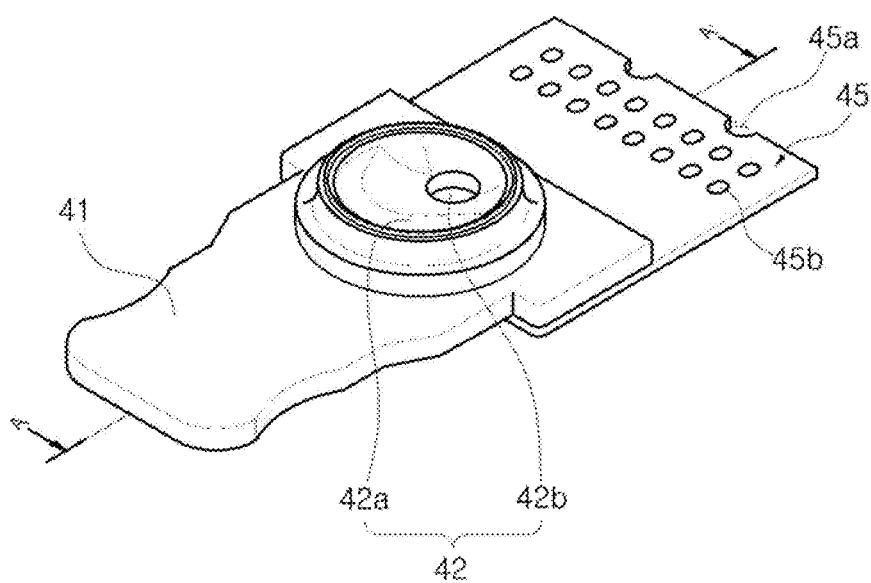
FIG. 4 is a view illustrating a fluid analysis cartridge according to an exemplary embodiment.

FIG. 2 is a view illustrating a state in which the fluid analysis cartridge 40 according to an exemplary embodiment is uncoupled from the mounting member 32 of the fluid analysis device 1 to which the fluid analysis cartridge is coupled. FIG. 3 is a view illustrating a state in which the fluid analysis cartridge 40 according to an exemplary embodiment is coupled to the mounting member of the fluid analysis device to which the fluid analysis cartridge is coupled during analysis. FIG. 4 is a view illustrating the fluid analysis cartridge according to an exemplary embodiment.

As shown in FIG. 1 through FIG. 3, the fluid analysis cartridge 40 may be inserted into the mounting member 32 of the fluid analysis device 1. The mounting member 32 may include a seating part 32c on which the fluid analysis cartridge 40 is settled and a supporting part 32f used to support the mounting member 32 in the fluid analysis device 1. The supporting part 32f extends to both sides of a body 32e of the mounting member 32 and the seating part 32c may be provided at a central portion of the body 32e. A slit 32d may be formed at a rear of the seating part 32c used to prevent an error from occurring when the inspection result of the fluid specimen of the inspection substrate 45 is measured.

The mounting member 32 includes contact parts 32a and 32b which are in contact with the fluid analysis cartridge 40, and the inspection substrate 45 of the fluid analysis cartridge 40 may include a dent part 45a (see FIG. 4) having shapes corresponding to the contact parts 32a and 32b. Thus, the dent part 45a may be in contact with the contact parts 32a and 32b. According to an exemplary embodiment, two dent parts 45a are provided, and two contact parts 32a and 32b may be formed to correspond to the dent parts 45a.

The fluid analysis cartridge 40 includes a housing 41 forming an outer appearance thereof and the inspection substrate 45 in which the fluid and the reagent are in contact with each other and the fluid reacts with the reagent.

The housing 41 may include a gripping part configured to support the fluid analysis cartridge 40 and to enable the user to grip the fluid analysis cartridge 40. The gripping part has a streamlined protrusion shape so that the user stably grips the fluid analysis cartridge 40, while a distal end of the fluid analysis cartridge 40, and corresponding inspection substrate 45 disposed adjacent to contact parts 32 and 32b.

In addition, a fluid supplying part 42 to which the fluid specimen is supplied may be provided in the fluid analysis cartridge 40. The fluid supplying part 42 may include a supplying hole 42b through which the fluid specimen is introduced into the inspection substrate 45, and a supply assistance part 42a configured to assist a supply of the fluid. The fluid which may be inspected in the fluid analysis device 1 is supplied to the fluid supplying part 42. For example, the subject fluid may be body fluids including blood, tissue-liquid, lymphatic fluid; biological samples such as saliva, urine and the like, and environmental samples for a soil management or a water quality management. However, the subject fluid is not limited to these fluids.

As shown in FIG. 3, the supplying hole 42b may be formed in a circular shape. However, the supplying hole is not limited thereto and may be formed in a polygonal shape. The user may drop the fluid specimen on the fluid supplying part 42 using a tool such as a pipette or a spuit. The supply assistance part 42a disposed around the supplying hole 42b is inclined toward the supplying hole 42b so that the fluid specimen dropped around the supplying hole 42b may flow into the supplying hole 42b. Specifically, in a case in which the user does not accurately drop the fluid specimen in the supplying hole 42b and the fluid specimen is dropped around the supplying hole 42b, the fluid specimen dropped around the supplying hole 42b may flow into the supplying hole 42b by a slope of the supply assistance part 42a.

In addition, the supply assistance part 42a contributes not only to supply the fluid specimen, but also to prevent a contamination of the fluid analysis cartridge 40 caused by the fluid specimen which is erroneously supplied. Specifically, even though the fluid specimen is not accurately introduced into the supplying hole 42b, since the supply assistance part 42a prevents the fluid specimen from flowing toward the inspection substrate 45 or the gripping part, it is possible to prevent a contamination of the fluid analysis cartridge 40 caused by the fluid specimen and to protect a user from being in contact with the potentially harmful fluid specimen.

As shown in the drawings, the fluid supplying part 42 has only one supplying hole 42b. However, exemplary embodiment is not limited thereto, and a plurality of supplying holes may be provided on the fluid supplying part. In a case in which the fluid supplying part is provided with a plurality supplying holes, the inspections for a plurality of different fluid specimens can be simultaneously performed in one fluid analysis cartridge. Here, the plurality of fluid specimens may be of the same kind but obtained from different sources, may be of different kinds and obtained from different sources, or may be of the same kind and obtained from the same source, but in different states.

As described above, since, in some case, the housing 41 has the shape implementing a specific function and is in contact with the fluid specimen, the housing 41 may be formed of materials which are easily formed and are chemically and biologically inactive. For example, the housing 41 may be formed of various materials including acrylate such as polymethyl methacrylate (PMMA), polysiloxane such as polydimethylsiloxane (PDMS), polyethylene such as polycarbonate (PC), linear low density polyethylene (LLDPE), low density polyethylene (LDPE), medium density polyethylene (MDPE) and high density polyethylene (HDPE), plastic material such as polyvinyl alcohol, very low density polyethylene (VLDPE), polypropylene, acrylonitrile butadiene styrene (ABS), cyclic olefin copolymer (COC), glass, mica, silica, semiconductor wafer and the like However, the above substances are only examples of the substance which may be employed as the material for the housing 41, and an exemplary embodiment is not limited thereto. If the substance has the chemical and biological stability and machinability, any substance may be utilized as the material for the housing 41 according to an exemplary embodiment.

The inspection substrate 45 may be coupled or attached to the fluid analysis cartridge 40. The fluid introduced via the fluid supplying part 42 is introduced into the inspection substrate, such that this fluid may react with the reagent to perform an inspection. The inspection substrate 45 includes an inspection part 45b, and the reagent reacting with the fluid is accommodated in the inspection part 45b.

Figure 5:
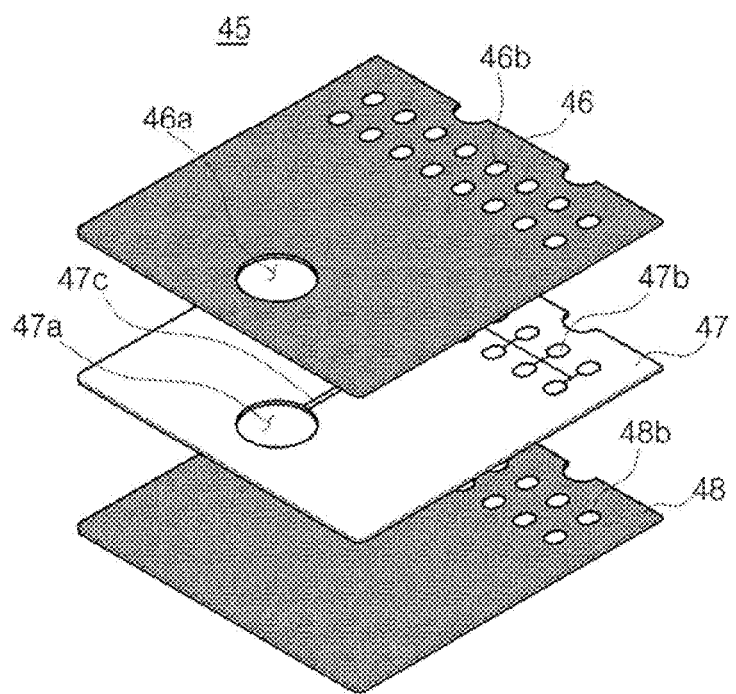
FIG. 5 is an exploded perspective view of an inspection substrate of a fluid analysis cartridge according to an exemplary embodiment.

FIG. 5 is an exploded perspective view of the inspection substrate of the fluid analysis cartridge according to an exemplary embodiment.

As shown in FIG. 5, the inspection substrate 45 of the fluid analysis cartridge 40 according to an exemplary embodiment may be formed by attaching three layers 46, 47 and 48. Three layers 46, 47 and 48 may be divided into an upper layer 46, an intermediate layer 47 and a lower layer 48. The upper layer 46 and the lower layer 48 may be coated with light shielding ink to protect the fluid specimen, which is flowing into the inspection part 45b, from external light or to prevent an occurrence of the error when an optical characteristic is measured in the inspection part 45b.

The upper layer 46 and the lower layer 48 may have thicknesses of 10 μm to 300 μm, respectively, and the intermediate layer 47 may have a thickness d of 50 μm to 300 μm.

A film used to form the upper layer 46 and the lower layer 48 of the inspection substrate may be selected from polyethylene film such as linear low density polyethylene (LLDPE), low density polyethylene (LDPE), medium density polyethylene (MDPE) and high density polyethylene (HDPE); polypropylene (PP) film; polyvinyl chloride (PVD) film; polyvinyl alcohol (PVA) film; polystyrene (PS) film; and polyethyleneterephthalate (PET) film. However, the above-described films are only examples of the film which may be employed as the film for the upper and lower layers. If the film is chemically and biologically inactive and has the machinability, any film may be used as the film forming the upper layer 46 and the lower layer 48 of the inspection substrate 45.

Unlike the upper layer 46 and the lower layer 48, the intermediate layer 47 of the inspection substrate 45 is formed of a porous sheet. An example of the porous sheet which may be used as the intermediate layer 47 may be at least one of cellulose acetate, nylon 6.6, nylon 6.10 and polyethersulfone. Since the porous sheet is provided as the intermediate layer 47, the intermediate layer itself serves as a vent and enables the fluid specimen to be moved in the inspection substrate 45 without a separate driving source. In addition, if the fluid specimen is a hydrophilic fluid, the intermediate layer 47 may be coated with a hydrophobic solution in order to prevent the fluid specimen from permeating the intermediate layer 47. This will be described later.

An inlet part 46a through which the fluid specimen is introduced is formed on the upper layer 46, and a region 46b corresponding to the inspection part 45b may be transparent. Also, a region 48b of the lower layer 48, which corresponds to the inspection part 45b, may be transparent in order to measure an absorbance of the reaction occurring in the inspection part 45b, that is, an optical characteristic.

An inlet part 47a through which the fluid specimen is introduced is also formed on the intermediate layer 47, and the inlet part 46a of the upper layer 46 and the inlet part 47a of the intermediate layer 47 overlap to form an inlet part 44 of the inspection substrate 45. Various reactions for the fluid analysis may occur in the inspection substrate 45. In a case in which blood is used as the fluid specimen, by accommodating the reagent, which reacts with a specific ingredient (in particular, plasma) of the blood to generate a color or to be tarnished, it is possible to optically detect the color generated in the inspection part 45b and to digitize the detected color. Using the above numerical value representing the color within the inspection part, it is possible to ascertain whether or not there is the specific ingredient in the blood and/or a ratio of the specific ingredient.

Furthermore, the intermediate layer 47 may include a flow passage 47c configured to connect the inlet part 47a and an inspection part 47b.

Figure 6:
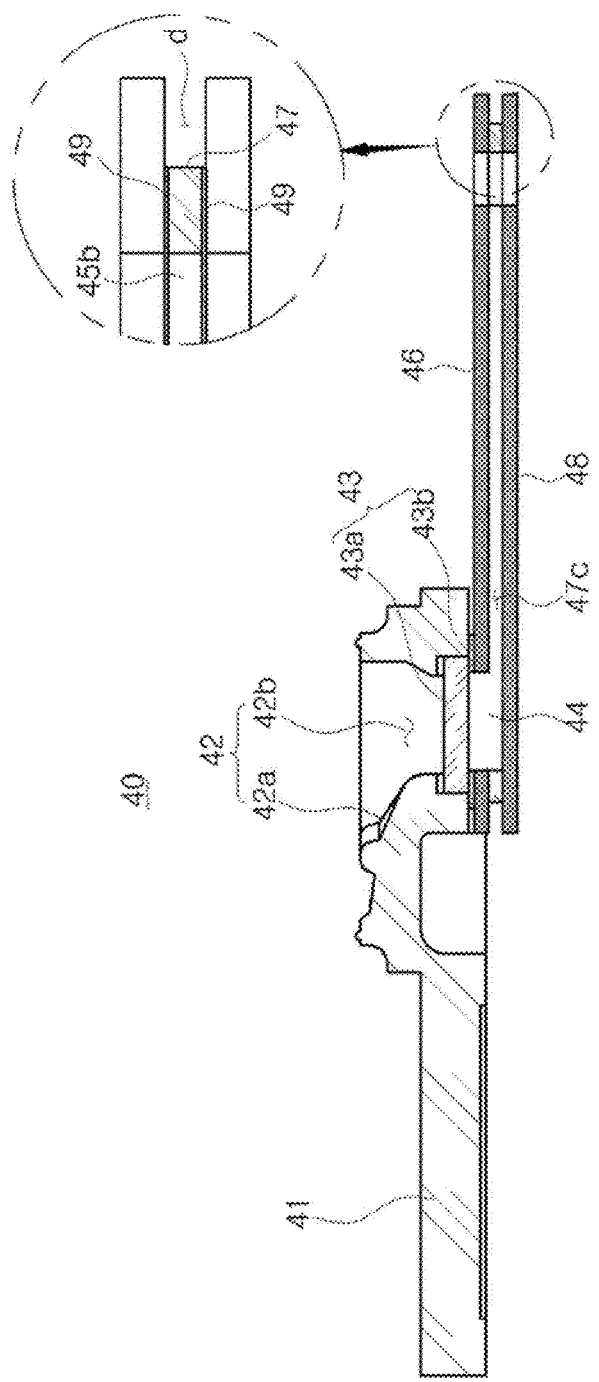
FIG. 6 is a cross-sectional view taken along the line A-A' of FIG. 4 and showing an inspection substrate of a fluid analysis cartridge.

FIG. 6 is a cross-sectional view taken along the line A-A' in FIG. 4 and showing the inspection substrate of the fluid analysis cartridge.

The fluid analysis cartridge 40 may be formed in such a way that the inspection substrate 45 is bonded to a lower portion of the housing 41. More specifically, the inspection substrate 45 may be bonded to a lower portion of the fluid analysis cartridge 40 on which the supplying hole 42b is provided. A pressure sensitive adhesive (PSA) may be used to bond the inspection substrate 45 to the housing 41. Here, the pressure sensitive adhesive can be rapidly adhered to an adherend with a low pressure, which is similar to a finger pressure, at room temperature, and does not generate a cohesive failure when an adhesive layer is removed from the adherend, and does not leave an adhesive residue on a surface of the adherend. However, the housing 41 and the inspection substrate 45 are not necessarily bonded to each other by the pressure sensitive adhesive. The housing 41 and the inspection substrate 45 may be attached to each other by a double-sided tape or can be coupled to each other by inserting the inspection substrate into a groove of the housing.

The fluid specimen introduced via the supplying hole 42b passes through a filtering part 43 and is then introduced into the inspection substrate 45. The filtering part 43 may be inserted into the supplying hole 42b of the housing 41.

The filtering part 43 may include at least one porous membrane having a plurality of pores to filter out substances in the fluid specimen, which has a size of a predetermined size or more. According to the one embodiment, the filtering part 43 may include double-layered filters. As one example, a first filter 43a may be formed of glass fiber, non-woven fabric or absorbent filter. A second filter 43b may be formed of polycarbonate (PC), polyethersulfone (PES), polyethylene (PE), polysulfone (PS) or polyarylsulfone (PASF).

In a case in which the filtering part 43 is formed as the double-layer filter, the fluid specimen passed through the upper-layer filter is filtered by the lower-layer filter once more. In addition, in a case in which a large quantity of particles, each of which having a size larger than a pore of the filtering part 43, are introduced, it is possible to prevent the filtering part 43 from tearing or from being damaged. However, the structure of the filtering part is not limited thereto, but may include a triple-layer filter or more-layered filter. In this case, a filtering function for the fluid specimen is more powerful and a stability of the filtering part 43 is also more enhanced. The filters constituting the filtering part 43 may be secured to each other by an adhesive material (not shown) such as a double-sided tape.

In the inspection substrate 45, the inlet part 44 through which the fluid specimen passed through the filtering part 43 is introduced, the flow passage 47c through which the introduced fluid specimen flows, and the inspection part 45b in which the fluid specimen reacts with the reagent may be provided.

The upper layer 46, the intermediate layer 47 and the lower layer 48 may be coupled to each other by a double-sided tape 49. More specifically, the double-sided tapes 49 are attached to an upper face and a lower face of the intermediate layer 47, respectively so that upper layer 46, the intermediate layer 47 and the lower layer 48 are coupled to each other.

Figure 7:
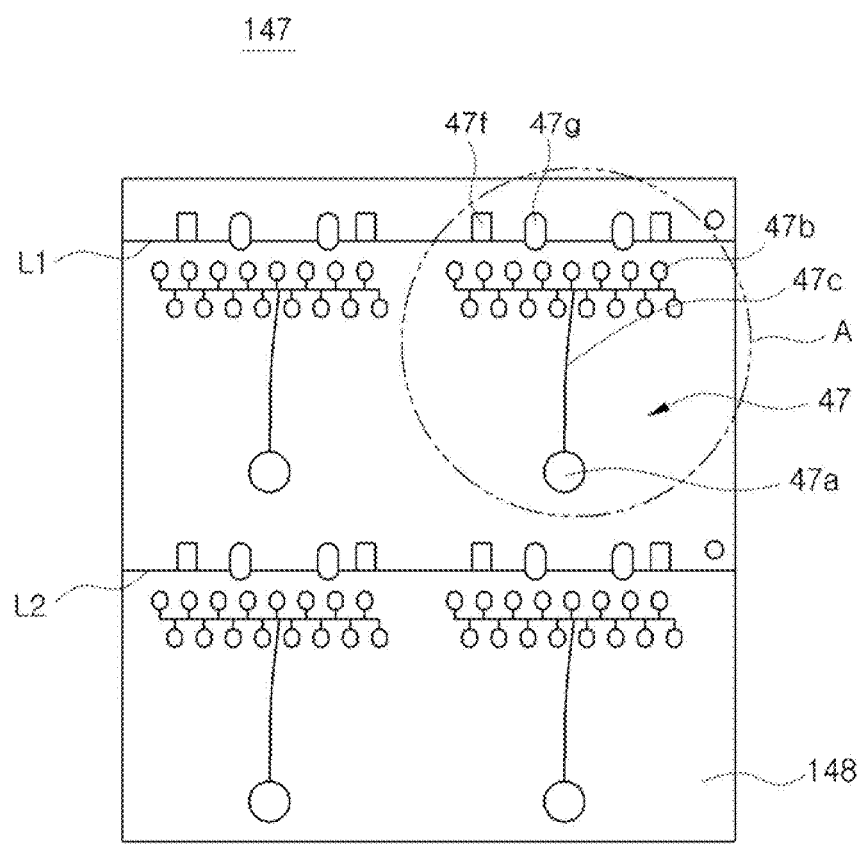
FIG. 7 is a view showing a fluid analysis sheet according to an exemplary embodiment.
Figure 8:
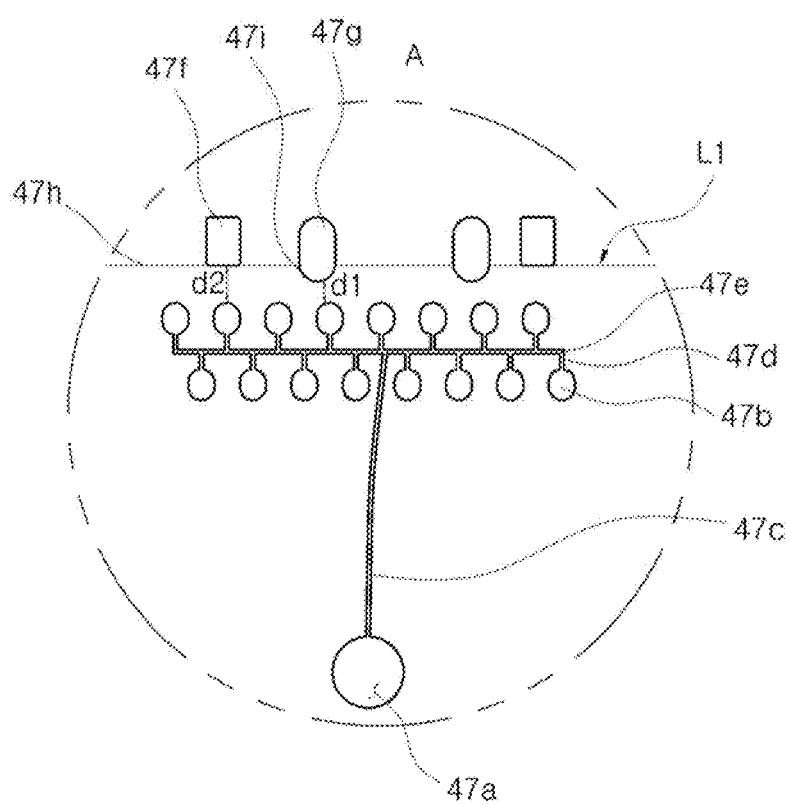
FIG. 8 is an enlarged view of portion "A" in FIG. 7.

FIG. 7 is a view illustrating a fluid analysis sheet according to an exemplary embodiment and FIG. 8 is an enlarged view of portion "A" of FIG. 7.

As shown in FIG. 7 and FIG. 8, the intermediate layer 47 of the inspection substrate 45 according to an exemplary embodiment may be produced by cutting-out a fluid analysis sheet 147 which includes the pattern of several intermediate layers 47.

The intermediate layer 47 may include a flow passage structure including the plurality of inlet parts 47a through which the fluid is introduced and the inspection part 47b in which the fluid is introduced to react with the reagent. The first flow channel 47c may be provided between the inlet part 47a and the inspection part 47b to connect the inlet part and the inspection part. In addition, a second flow channel 47e and a third flow channel 47d may be provided to connect the inspection parts 47b. The second flow passage 47e is connected to the first flow passage 47c to connect the inspection parts 47b to the second flow passage. The third flow passage 47d extends from at least one portion of the second flow passage 47e and is connected to one inspection port in the part 47b.

The fluid analysis sheet 147 may be provided with a plurality of units constituting the intermediate layer 47. Two units are arranged per one column and two columns are provided in the fluid analysis sheet 147 of FIG. 7. However, the above structure is merely one embodiment, and in an exemplary embodiment, the number of the unit or the number of the column included in one fluid analysis sheet 147 is not limited.

A surface of the fluid analysis sheet 147 may be coated with the hydrophobic solution for preventing a hydrophilic fluid from being spread in the inspection substrate 45. A process for coating the fluid analysis sheet 147 with the hydrophobic solution will be described later.

In an exemplary embodiment, one unit of the fluid analysis sheets forms one intermediate layer 47. The fluid analysis sheet 147 should can be cut-out, to form a cut-out part. The cut-out part may be cut-out with respect to a dead zone of the unit. For convenience, the cut-out part adjacent to the inspection part 47b is defined as a first distal end L1, and the cut-out part adjacent to the inlet part 47a is defined as a second distal end L2. Specifically, in FIG. 7, the first distal end L1 means an upper end of the inspection part 47b and the second distal end L2 means a lower end of the inlet part 47a. The line L2 designates a second row 148 of the fluid analysis sheet 147, from which two intermediate layers 47 may be formed.

The first distal end L1 may include at least one dent part 47g dented inward toward the inlet part 47a. The dent part 47g may be coupled to or coincide with the upper layer 46 and the lower layer 48 to form the dent part 45a of the inspection substrate 45.

The at least one dent part 47g may be arranged to have a certain pattern. According to an exemplary embodiment, the dent part 47g may be formed in a circular shape. However, an exemplary embodiment is not limited thereto, and it is possible to provide a polygonal dent part such as a quadrangular dent part. A minimum distance d1 between the first distal end L1 and the flow passage structure may be at least 1 mm. More specifically, in an exemplary embodiment in which the dent part 47g is formed in the circular shape, a minimum distance between the dent part 47g and the flow passage structure may be at least 1 mm. In a case in which the dent part is formed in a quadrangular shape, however, the minimum distance between the dent part and the flow passage structure may be at least 2 mm.

According to an exemplary embodiment, the first distal end L1 may be formed in a curved-shaped first contact part 47i and a linear-shaped second contact part 47h. The first contact part 47i may form the dent part 47g. According to an exemplary embodiment, the first contact part 47i may be formed by a circular hole forming the dent part 47g. In addition, at least one portion of the second contact part 47h may be formed by a quadrangular hole 47f.

The minimum distance d1 between the circular hole and the flow passage structure may be 1 mm. A minimum distance d2 between the quadrangular hole 47f and the flow passage structure may be 2 mm. Specifically, the minimum distance d1 between the circular hole and the inspection part 47b may be 1 mm. The minimum distance d2 between the quadrangular hole 47f and the inspection part 47b may be 2 mm. In the case of the quadrangular hole 47f, a cut-out is performed along a side of the quadrangular hole 47f, the minimum distance between the quadrangular hole and the flow passage structure may be greater than that between the circular hole and the flow passage structure If the minimum distance d1 between the dent part 47g and the flow passage structure is less than 1 mm, a distance between the dent part 47g and the inspection part 47b is short so that, when the fluid specimen is introduced into the inspection part 47b, the fluid specimen can be leaked to the dent part 47g by an external pressure. In addition, in a case in which the minimum distance d1 between the dent part 47g and the flow passage structure is less than 1 mm, a strength of the inspection substrate 45 is weakened so that the inspection substrate 45 is fragile. According to an exemplary embodiment, however, it is possible to prevent the fluid specimen from leaking and the inspection substrate 45 from breaking In addition, the dent part 47g is provided at the first distal end L1 and the first distal end L1 is provided to space a certain distance from the flow passage structure. Thus, in a case in which a first fluid analysis film (not shown) constituting the upper layer 46, the fluid analysis sheet 147 constituting the intermediate layer 47 and a second fluid analysis film (not shown) constituting the lower layer 48 are coupled to each other to form a coupled body and the coupled body is then cut-out to form one inspection substrate 45, the intermediate layer 47 is located inside with respect to the upper layer 46 and the lower layer 48. Therefore, the double-sided tape 49 adhered to the intermediate layer 47 is in contact with the contact parts 32a and 32b of the fluid analysis device 1 so that it is possible to prevent foreign substances from being generated and to reduce of inspection errors.

Figure 9:
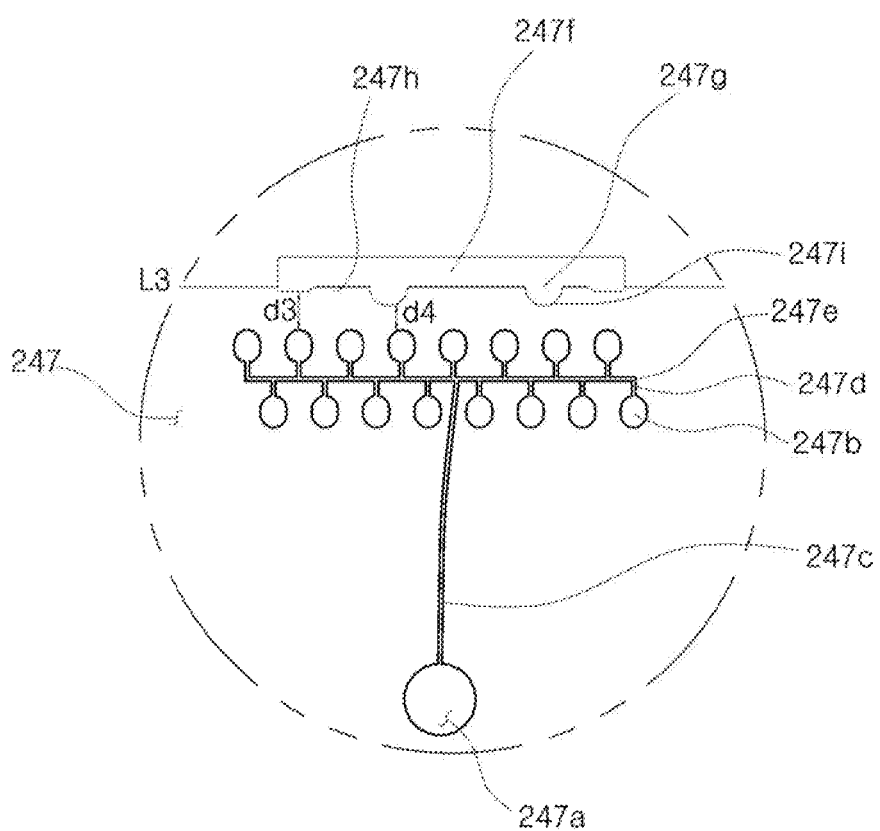
FIG. 9 is a view showing one unit of a fluid analysis sheet according to an exemplary embodiment.

FIG. 9 is a view illustrating one unit of a fluid analysis sheet according to an exemplary embodiment.

An intermediate layer 247 according to an exemplary embodiment shown in FIG. 9 may include an inspection part 247b, an inlet part 274a, a first flow channel 247c, a second flow channel 247e, and a third flow channel 247d.

According to an exemplary embodiment, as shown in FIG. 9, a first contact part 247i formed at a first distal end L3 is formed in a curved shape and may be formed at an inner side of the first distal end L3 to form a dent part 247g. In addition, according to an exemplary embodiment, unlike the embodiment shown in FIG. 8 and FIG. 9 in which the circular hole and the quadrangular hole are separately formed, the first contact part 247i and a second contact part 247h are provided on one pattern 247f. The dent part 247g corresponding to the first contact part 247i may be formed such that the dent part is adjacent to the flow passage structure. More specifically, a minimum distance d3 between the dent part 247g and an inspection part 247c may be 1 mm. In addition, a minimum distance d4 between the second contact part 247h and the inspection part 247c may be 2 mm.

In this case, the shape obtained when the first distal end L3 is cut-out is the same as that in the embodiment shown in FIG. 7 and FIG. 8. Therefore, it is possible to prevent a breakage of the inspection substrate 45 and a leakage of the fluid specimen. In addition, since the intermediate layer 247 is located inside with respect to the upper layer 46 and the lower layer 48, it is possible to prevent foreign substances from being generated on the fluid analysis device 1 due to the double-sided tape 49 attached to the intermediate layer 247.

As described above, the fluid analysis sheet 147 constituting the intermediate layer of the fluid analysis cartridge according to one embodiment of the invention is coated with the hydrophobic solution.

The fluid analysis sheet 147 may be wound around a coating roll and then coated with the hydrophobic solution. The coating roll includes a rotational shaft configured to move the fluid analysis sheet and a coating part around which the fluid analysis sheet 147 is wound. The coating part may include a coating layer formed by coating a surface thereof with fluorinated coating solution. More specifically, the coating layer on the surface of the coating part may be a coating layer formed of at least one of polytetrafluoro ethylene (PTFE), polychlorotrifluoro ethylene (PCTFE), polyvinylidene fluoride (PVDF) and polyvinyl fluoride (PVF).

According to the above process, the fluid analysis sheet 147 may be coated with the hydrophobic solution.

More specifically, a coating device for performing a hydrophobic coating process for the fluid analysis sheet 147 includes a main roll around which the fluid analysis sheet 147 is wound, a first coating container in which a first coating process is carried out, and a second coating container in which a second coating process is carried out.

In addition, the coating device may include drying racks for drying the fluid analysis sheet after the first and second coating processes are performed, respectively. Thus, the fluid analysis sheet 147 may pass through a first drying rack after the first coating process is performed and a second drying rack after the second coating process is performed to dry the coated portion. At this time, the coating device may be further provided with at least one guide roll for guiding a movement of the fluid analysis sheet, and may be further provided with a separate roll around which the fluid analysis sheet 147 can be wound after the coating process is performed.

Two coating rolls, that is, a first coating roll and a second coating roll may be received in the first coating container. The first coating roll and the second coating roll may be received such that the first and second coating rolls are immersed in the hydrophobic solution for a hydrophobic coating process. Performing the first coating process using two coating rolls of the first coating roll and the second coating roll is to allow the fluid analysis sheet 147 to be immersed in the hydrophobic solution for long time, as a result, the fluid analysis sheet 147 is sufficiently coated with the hydrophobic solution.

At least one of fluorinated acrylic copolymer, fluorocarbon, silicone and fluorocarbon-silicon coupling agent may be used as the hydrophobic solution.

After performing the first coating process in the first coating container and a first drying process on the first drying rack, the second coating process may be performed in the second coating container.

Like the first coating container, two coating rolls, that is, a third coating roll and a fourth coating roll may be received in the second coating container. The third coating roll and the fourth coating roll may be received such that the third and fourth coating rolls are immersed in the hydrophobic solution for the hydrophobic coating process. Performing the second coating process using two coating rolls of the third coating roll and the fourth coating roll is to allow the fluid analysis sheet 147 to be immersed in the hydrophobic solution for long time, as a result, the fluid analysis sheet 147 is sufficiently coated with the hydrophobic solution.

After performing the second coating process, a second drying process may be performed on the second drying rack.

According to an exemplary embodiment, the first drying rack and the second drying rack are provided as one drying rack. However, the first drying rack and the second drying rack may be separately provided. A heater may be provided above the drying rack to supply heat with a certain temperature, and a fan may be also provided to transmit the heat to the drying rack.

According to the hydrophobic coating process for the fluid analysis sheet of an exemplary embodiment, by accommodating two coating rolls in one coating container and preventing a change of concentration of the hydrophobic solution in the coating container, the hydrophobic coating process may be stabilized.

Figure 10:
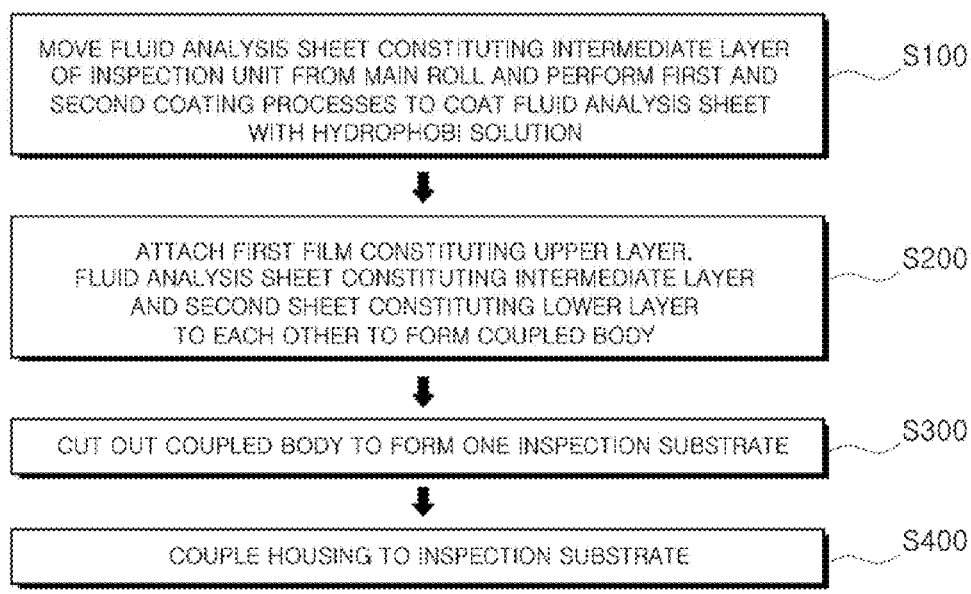
FIG. 10 is a flow chart schematically illustrating a method of manufacturing a fluid analysis cartridge according to an exemplary embodiment.

FIG. 10 is a flow chart schematically illustrating the method of manufacturing the fluid analysis cartridge according to an exemplary embodiment and FIG. 11 is a flow chart concretely illustrating the method of manufacturing the fluid analysis cartridge according to an exemplary embodiment.

As shown in FIG. 10 and FIG. 11, the fluid analysis cartridge according to an exemplary embodiment is manufactured by coating the fluid analysis sheet configured to form an intermediate layer of the inspection substrate with the hydrophobic solution (S100), attaching a first film constituting the upper layer, the fluid analysis sheet constituting the intermediate layer and the second film constituting the lower layer 48 to each other to form a coupled body (S200), cutting out the coupled body (S300) and coupling the housing to the inspection substrate (S400).

More specifically, when the coating process utilizing the hydrophobic solution is performed, the fluid analysis sheet configured to form the intermediate layer is moved from the main roll to perform the first coating process (S110). At this time, the fluid analysis sheet wound around the main roll is unwound from the main roll and is moved to the first coating container so that the coating process is performed by the hydrophobic solution in the first coating container. The first coating roll and the second coating roll are accommodated in the first coating container, and the fluid analysis sheet wound around the main roll is moved to the first coating roll and the second coating roll and is then coated with the hydrophobic solution.

After the first coating process is performed, the first drying process is carried out (S101). The fluid analysis sheet may be moved to the first drying rack to perform the first drying process.

Then, the second coating process is performed on the fluid analysis sheet (S102). The second coating process is performed by the hydrophobic solution in the second coating container. The third coating roll and the fourth coating roll are accommodated in the second coating container, and the third coating roll and the fourth coating roll are immersed in the hydrophobic solution. Thus, the fluid analysis sheet is coated with the hydrophobic solution while passing successively through the third coating roll and the fourth coating roll.

After the second coating process is performed, the second drying process is carried out (S103). The fluid analysis sheet may be moved to the second drying rack to perform the second drying process.

Thereafter, the intermediate layer of the fluid analysis cartridge is formed of the fluid analysis sheet coated with the hydrophobic solution. Therefore, the first film constituting the upper layer, the fluid analysis sheet constituting the intermediate layer and the second film constituting the lower layer are attached to each other to form the coupled body (S200). The first film, the fluid analysis sheet and the second film may be attached to each other by the double-sided tape as described above.

The coupled body is then punched to form the inlet part through which the fluid specimen is introduced and the inspection part at which the inspection is performed (S201).

In order to form one inspection substrate, the coupled body is then cut out (S300). The housing is coupled to the inspection substrate (S400).

According to the fluid analysis sheet and the fluid analysis cartridge including the same according to an exemplary embodiment, it is possible to suppress a generation of foreign substances occurring when the fluid analysis sheet comes into contact with the fluid analysis device and can prevent the inspection substrate from being damaged during the manufacturing process.

In addition, according to the method of manufacturing the fluid analysis cartridge according to an exemplary embodiment, it is possible to enhance the inspection reliability by improving the process for coating the fluid analysis sheet with the hydrophobic solution.

While exemplary embodiments have been described, it will be apparent to those skilled in the art that various changes and modifications may be made without departing from the spirit and scope of the inventive concept as defined in the following claims and their equivalents.

What is claimed is:

1. A fluid analysis sheet comprising:
   at least one cut out part configured to form an intermediate layer of an inspection substrate, the cut out part comprising:
   a flow passage structure including an inlet part in which a fluid is introduced, and an inspection part in which the fluid is introduced to react with a reagent; and
   wherein the cut out part is further configured to include a first end adjacent to the inspection part and a second end adjacent to the inlet part, and
   wherein a minimum distance between the first end and the inspection part of the flow passage structure is at least 1 mm, and wherein the minimum distance is the smallest straight line distance between the first end and any part of the flow passage structure where the fluid is introduced to react with a reagent.

2. The fluid analysis sheet of claim 1, wherein the first end comprises at least one dent part oriented toward the second end.

3. The fluid analysis sheet of claim 2, wherein the dent part is formed to have a pattern.

4. The fluid analysis sheet of claim 2, wherein the dent part is formed in a circular shape.

5. The fluid analysis sheet of claim 2, wherein the dent part is formed in a quadrangular shape.

6. The fluid analysis sheet of claim 1, wherein the first end comprises a first contact part formed in a curved shape and a second contact part formed in a linear shape.

7. The fluid analysis sheet of claim 6, wherein a minimum distance between the first contact part and the flow passage structure is at least 1 mm.

8. The fluid analysis sheet of claim 6, wherein a minimum distance between the second contact part and the flow passage structure is at least 2 mm.

9. The fluid analysis sheet of claim 1, wherein the fluid analysis sheet has a surface which is coated with a hydrophobic solution to prevent a hydrophilic fluid from being spread therein.

10. The fluid analysis sheet of claim 1, comprising a plurality of the cut out part arranged in at least one of: two columns and two rows.

11. The fluid analysis sheet of claim 1, wherein the fluid analysis sheet formed from a porous material.

12. A fluid analysis cartridge comprising:
    a housing including at least one supplying hole to supply a fluid specimen; and
    an inspection substrate coupled to the housing such that the fluid specimen introduced through the supplying hole is introduced to be inspected,
    wherein the inspection substrate comprises;
    an upper layer located at an upper side;
    a lower layer located at a lower side; and
    an intermediate layer located between the upper layer and the lower layer, and coupled to the upper layer and the lower layer such that at least a portion of outermost ends of the intermediate layer are located inside with respect to an edge of the upper layer and an edge of the lower layer.

13. The fluid analysis cartridge of claim 12, wherein the intermediate layer has a flow passage structure that includes an inlet part in which a fluid is introduced; and
    an inspection part in which the fluid is introduced to react with a reagent.

14. The fluid analysis cartridge of claim 13, wherein the first end of the intermediate layer is adjacent to the inspection part, and the first end is provided with a dent part oriented such that at least a portion of the dent part is dented inward from the first end.

15. The fluid analysis cartridge of claim 14, wherein the dent part is formed to have a pattern.

16. The fluid analysis cartridge of claim 15, wherein the dent part is formed in a circular shape and a minimum distance between the dent part and the flow passage structure is at least 1 mm.

17. The fluid analysis cartridge of claim 15, wherein the dent part is formed in a quadrangular shape and a minimum distance between the dent part and the flow passage structure is at least 2 mm.

18. The fluid analysis cartridge of claim 12, wherein a surface of the intermediate layer is coated with a hydrophobic solution to prevent a hydrophilic fluid from being spread therein.

19. The fluid analysis cartridge according to claim 12, wherein the intermediate layer is formed from a porous material; and
    the upper layer and the lower layer are formed from a chemically and biologically inactive film.

20. A method of manufacturing a fluid analysis cartridge comprising: an inspection substrate in which a fluid is inspected, the inspection substrate including an upper layer, an intermediate layer and a lower layer, and the fluid analysis cartridge further including a housing coupled to the inspection substrate, the method comprising;
    moving a fluid analysis sheet constituting the intermediate layer of the inspection substrate from a main roll;
    performing first and second coating processes to coat the fluid analysis sheet with a hydrophobic solution;
    attaching an upper film constituting the upper layer, the fluid analysis sheet constituting the intermediate layer and a lower film constituting the lower layer to each other to form a coupled body;
    cutting out the coupled body to form one inspection substrate; and
    coupling the housing to the inspection substrate, wherein the coupled body is cut off such that the intermediate layer is located inside with respect to at least one outermost edge of the upper layer and at least one edge of the lower layer.

21. The method of claim 20, wherein the fluid analysis sheet is wound around a first coating roll and a second coating roll when at least one of the first and second coating processes is performed.

22. The method of claim 20, comprising performing a first drying process and a second drying process after each of the first and second coating process is performed.

23. The method of claim 20, wherein, the hydrophobic solution comprises at least one of fluorinated acrylic copolymer, fluorocarbon, silicone and a fluorocarbon-silicon coupling agent.

24. The method of claim 20, wherein the coupled body is formed by attaching double-sided tapes on an upper surface and a lower surface of the fluid analysis sheet.

25. The method of claim 20, wherein the intermediate layer includes a dent part oriented such that at least a portion of the dent part is dented inward from an edge so as to be formed to be located inside with respect to an edge of the upper layer and an edge of the lower layer, and the method comprises forming the dent part before the coupled body is cut.

* * * * *